United States Patent [19]

Lippes

[11] Patent Number: 4,821,732
[45] Date of Patent: Apr. 18, 1989

[54] METHOD FOR MONITORING FETAL-MATERIAL CIRCULATION TIME

[76] Inventor: Jack Lippes, 100 Lincoln Pkwy., Buffalo, N.Y. 14222

[21] Appl. No.: 41,470

[22] Filed: Apr. 23, 1987

[51] Int. Cl.$^4$ .............................................. A61B 5/00
[52] U.S. Cl. .................................... 128/632; 128/668; 128/716
[58] Field of Search ................ 128/668, 698, 632–633, 128/670–671, 716, 1 R, 630, 204.23; 604/23

[56] References Cited

U.S. PATENT DOCUMENTS

| | | | |
|---|---|---|---|
| 3,621,844 | 11/1971 | Hayashi et al. | 128/698 |
| 4,220,158 | 9/1980 | Delpy et al. | 128/632 |
| 4,346,710 | 8/1982 | Thanawalla et al. | 128/DIG. 24 |
| 4,445,515 | 5/1984 | DiResta | 128/632 |
| 4,537,197 | 8/1985 | Hulka | 128/633 |

FOREIGN PATENT DOCUMENTS

| | | | |
|---|---|---|---|
| 0072235 | 2/1983 | European Pat. Off. | 128/716 |
| 0624602 | 9/1978 | U.S.S.R. | 128/668 |

*Primary Examiner*—Kyle L. Howell
*Assistant Examiner*—Angela D. Sykes
*Attorney, Agent, or Firm*—Thomas C. Saitta

[57] ABSTRACT

A method of monitoring fetal and maternal circulatory times as an indicator of fetal distress, involving the detection and measurement of the concentration of a gas transdermally diffused through the skin of the mother and the fetus, subsequent to inhalation of the gas by the mother. Time and concentration values are then compared to provide indications of distress in the fetus.

19 Claims, 1 Drawing Sheet

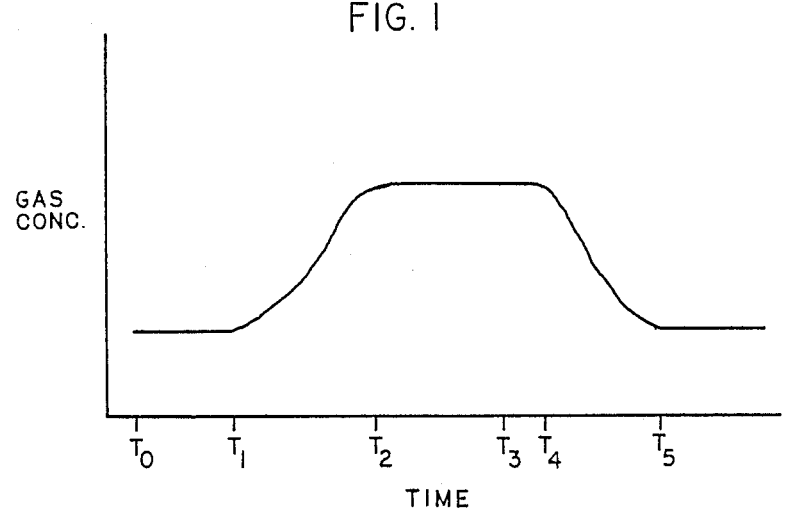

METHOD FOR MONITORING FETAL-MATERIAL CIRCULATION TIME

BACKGROUND OF THE INVENTION

This invention pertains to a method for monitoring fetal-maternal circulation time and fetal-maternal respiratory kinetics as an indicator of the condition of a fetus during child-birth. More particularly, the method involves measurement of maternal circulation time and maternal-fetal circulation time by detecting transdermal respiration, at a selected point on the skin of the mother and at a point on the fetal scalp, of an identifiable gas inhaled by the mother. The method employs a monitoring system of a gas analyzer or detector comprising a mass spectrometer or an atomic absorption spectro-photometer connected to a sniffer probe attached by suction to the maternal and fetal skin.

The time during which the mother is in labor prior to birth is a critical period with regard to the health of the fetus. It is important to have immediate indication of any problem relating to the condition of the fetus caused by pathology of or changes in the utero-placental-fetal unit or because of some medical problem in the fetus itself. Difficulties in this unit can cause permanent damage or even threaten the life of the fetus. Examples of medical problems which can be encountered are blockage of the umbilical cord, placental dysfunction or abruption of the placenta, resulting in partial or total loss of oxygen to the fetus. In the mother, cardiac failure or obstructive pulmonary disease can reduce oxygen supply to the fetus. Physicians must be in a position to make rapid decisions during labor to protect the fetus from harm, including the decision of interrupting the natural birth process by performing a caesarian section.

There are currently several methods used to monitor the fetal condition during labor. One such method in common use involves an electronic fetal monitor (EFM). Examples of EFM methods and apparati are shown in U.S. Pat. Nos. 3,599,628, 3,367,323 and 3,409,737. In general, an EFM uses a recorder to register simultaneously the fetal heartbeat and uterine contractions. Ominous patterns, such as loss of beat to beat variability, sometimes can be discerned before labor. This is referred to as a non-stress test. Frequently, ominous patterns of the fetal heart rate are noticed during or immediately after contractions, for example, delayed decelerations or variable decelerations of the fetal rate. These patterns indicate possible trouble for the fetus. The evaluation of these ominous patterns can be difficult and the information provided is subject to misinterpretation. Secondary tests are often needed to accurately determine if fetal distress is actually occurring. One secondary method is to sample blood from an incision in the fetal scalp and measure the blood pH to diagnose fetal acidosis, a definite threat to the fetus. Alternatively, subcutaneous oxygen probes can be inserted to determine scalp $pO_2$, although the technology to measure scalp $pO_2$ is not sufficiently developed at this time to be in general use. These invasive methods create further hazards to the fetus by increasing the chances of infection. Because the ominous EFM patterns must be subjectively evaluated, it is believed that a much greater number of caesarian births are performed than are necessary.

Methods and apparati for measuring diffusion through the skin of gases insoluble in the blood stream are known in the literature. The gas can be inhaled or injected intravenously. An example of one type of transcutaneous physiological sensor apparatus is shown in U.S. Pat. No. 4,334,541.

Numerous gas detectors and analyzers are known, for example, the Varian Porta-Test (TM) helium leak detector 938-41 or the Inficon series mass spectrometer gas analyzers. These are used primarily in industry to test the security of tanks for gas leaks.

SUMMARY OF THE INVENTION

In broad terms, the invention is a method for monitoring fetal-maternal circulation time by monitoring transdermal diffusion of a particular gas taken by the mother. The transdermal diffusion is detected at a selected site on the skin of the mother and at a site on the scalp of the fetus. Normal parameters can be obtained and with periodic or continual monitoring, fetal or maternal distress, as indicated by a change in the parameters, can be observed. The method involves use of an apparatus which includes a gas detector or gas analyzer connected to a suction cup attached to the skin.

With more particularity, the method involves inhalation of a predetermined concentration of a gas insoluble in the blood stream and detectable by a gas detector or analyzer after transdermal respiration. The gas analyzer suction cup is attached to a selected spot on the skin of the mother and at time zero the gas is inhaled by the mother. After some time period, the gas is diffused through the mother's skin and detected by the analyzer, thus providing a time value for maternal circulation. Maternal circulation is here defined as trachea-lung-heart-skin circulation. The inhalation of the rare gas is stopped and the mother's respiratory system is allowed to return to equilibrium. The suction cup is attached to the fetal scalp, the mother again inhales the gas and the time value for first detection is determined. This provides the maternal-fetal circulation time value, which is defined as the trachea-lung-heart-uterus-placenta-fetal heart-fetal skin circulation. The difference between these two values provides an indicator of utero-placental-fetal circulation time, herein called fetal circulation time. Upon determination of the normal time values, the mother and fetus can be periodically or continuously monitored to detect any significant change in any of the time values, a lengthening of fetal circulation time indicating probable fetal distress.

In another embodiment, the method involves continual monitoring of the transdermal diffusion of the inhaled, predetermined concentration of gas, such that a record is obtained for gas concentration over the time period from first detection onward. At some time period after inhalation, the level of the gas in the circulatory system of the mother and fetus reaches a maximum concentration and, correspondingly, a maximum concentration of the gas would be detected through the skin of the mother and fetus by the gas analyzer. Both the maximum concentration value and the time to reach maximum concentration would reflect the condition of maternal-fetal circulation.

In another embodiment, the method involves the detection of the decrease in transdermal diffusion after gas inhalation is discontinued.

In another embodiment, the method can be used to analyze the transdermal diffusion of normal physiological gases, e.g. carbon dioxide and oxygen, to determine nondistress values for mother and fetus. Thereafter, any decrease in normal fetal oxygen transdermal diffusion values or any increase in fetal carbon dioxide transdermal diffusion values would indicate fetal distress.

With more particularity, the apparatus involved in the method comprises a small suction cup connected by a flexible tube to the detector mechanism of a gas analyzer incorporating a mass spectrometer. A small suction is maintained to insure optimum attachment to the skin, to preclude ambient air from entering the cup and to draw the diffused gas to the detector mechanism. The gas analyzer provides a record of concentration over time.

An object of this invention is to provide a method for monitoring the maternal and fetal condition during labor, in order to provide the physician with an indication of maternal or fetal distress.

Another object of this invention is to provide a method for monitoring maternal-fetal conditions which can be used in conjunction with existing methods, such as EFM, to provide for better interpretation of the information from these existing methods.

Another object of this invention is to provide a method for monitoring maternal-fetal conditions which is noninvasive and nonsurgical, thereby lessening the chances of infection to the fetus.

Another object of this invention is to provide a method for monitoring maternal-fetal conditions which supplies reliable information not subject to misinterpretation.

BRIEF DESCRIPTION OF THE DRAWING

FIG. 1 is a graph showing the concentration of diffused gas versus time, where continual monitoring is employed.

DESCRIPTION OF THE PREFERRED EMBODIMENTS

A small plastic suction cup in the shape of a cylinder approximately one centimeter in diameter and two centimeters in height, which is connected by a flexible tubular hose to a gas detector employing a mass spectrometer, is attached to the mother at a particular spot on her skin, for example, the thigh. The gas analyzer is of a type used to detect a rare gas, such as a Varian Porta-Test Helium Leak Detector 938-41. The gas analyzer is capable of tracking the concentration of the gas over time. The suction cup is attached and maintains contact with the skin by means of a slight but sufficient suction such that external air will not enter the cup and therefore only gases diffused transdermally are detected. The flexible tube connects the cup to the sniffer or detector mechanism of the gas analyzer and provides a conduit for the gas to reach said sniffer.

The mother is given a predetermined, measured concentration of a rare gas to inhale, e.g. helium, xenon, argon, krypton or neon. The rare gas is mixed with oxygen and nitrogen at a concentration much greater than its normal concentration in ambient air. For example, a mixture of 10% helium, 30% oxygen and 60% nitrogen can be used. The oxygen in the mixture should never be less than 20 percent. Upon inhalation the rare gas is taken down the trachea into the lungs, where it is absorbed into the blood stream, circulated by the heart and eventually diffused through the skin. At this time the gas analyzer detects the presence of the rare gas in the suction cup. The time span from first inhalation until first detection is noted and this value represents the normal maternal circulation time (trachea-lung-heart-skin) under non-distress conditions. A rare gas in a concentration much greater than in ambient air is used to insure that the gas detected within the suction cup is from transdermal diffusion and not merely from the presence of the gas in the ambient air.

After obtaining a maternal circulation value, the gas inhalation is discontinued and the concentration of rare gas in the mother's system is allowed to return to pre-inhalation levels, as measured by the gas analyzer. The suction cup is removed from the skin of the mother. Once the amniotic sac has broken or has been artificially ruptured, the suction cup can be attached to the fetal scalp or to the skin of a breech presentation without the necessity for an incision. The cup is attached and maintained in place by the slight suction. Again, the mother inhales the measured concentration of rare gas and the time from inhalation to first detection is noted. This value represents the normal maternal-fetal circulation time (trachea-lung-heart-uterus-placenta-fetal scalp) under non-distress conditions. These two values provide initial times for comparison with subsequent readings and the values should fall within known physiological ranges. The difference between the two initial values indicates a value for fetal circulation time (uterus-placenta-fetal scalp) under non-distress conditions.

At specific time intervals, for example, every fifteen minutes, the mother inhales the rare gas mixture and the maternal-fetal circulation time is noted. Comparison is then made of this value to the initial maternal-fetal circulation value. An increase in the value would be ominous and indicate possible distress to the fetus or to the mother. Upon detection of an ominous value, the maternal circulation time can be rechecked. This value will indicate whether the distress is caused by altered physiological conditions in the mother or, if the value matches the original initial value, will indicate that the problem is present with the utero-placental-fetal unit. The physician is then in a position to take measures to correct the problem and, if necessary, perform an emergency caesarian section to prevent damage to the fetus.

Mothers entering the hospital suspected of having fetal distress could immediately have maternal and fetal circulation times tested. The value would then be compared with known standard times, as determined through the use of this method, to assess the condition of the fetus.

Alternatively, the method can involve the use of two suction cups so that contact with both the maternal skin and fetal scalp can be maintained at the same time. Under this embodiment, the cup would not have to be removed from the mother to be placed on the fetus and vice-versa. The connection can be alternated at the gas analyzer or a two-way flow switch can be used to alternately open the flow to the gas analyzer from the proper suction cup. Likewise, two separate gas analyzers could be utilized so that simultaneous monitoring at both sites could be accomplished without need of alternating gas flow to the gas analyzer.

EXAMPLE 1

A pregnant sheep about seven days before term was anesthetized with Nembutal. Anesthesia was maintained with Halothene mixed with oxygen. A mixture of 90 percent oxygen and 10 percent helium was introduced through an endotracheal tube. A suction cup connected to a Varian Porta-Test Helium Detector 938-41 was attached to the skin of the sheep, such that a flow rate of approximately 0.00005 cc/sec at 6 millitors vacuum was maintained. First detection of transdermally diffused helium was 18 seconds after introduction of the helium-oxygen mixture. Administration of the helium-oxygen mixture was discontinued and transdermal helium concentration was allowed to return to pre-test levels. An incision was made in the sheep's abdomen and through the uterus. The lamb was delivered with umbilical cord still attached and functioning. The suction cup was then attached to the skin of the lamb and the sheep was again administered the helium-oxygen mixture. Helium was detected at the lamb's skin at 38 seconds. Therefore, the maternal-fetal circulation time was 38 seconds and subtraction of the maternal circulation time (18 seconds) from this value gives a fetal circulation time of 20 seconds. The helium-oxygen mixture was discontinued and helium concentration was allowed to return to equilibrium. In order to simulate fetal distress caused by a blockage of the umbilical cord, the cord was clamped and the sheep again given the helium-oxygen mixture. No helium was detected on the fetal skin, even after a period of six minutes.

As another embodiment of the invention, the method involves administration of the rare gas mixture continuously over a time period, one hour for example, and monitoring the concentration of the rare gas detected in the suction cup over the period of time starting from first inhalation of the rare gas and continuing through first detection until a maximum value is reached. This value will form a concentration plateau while the gas mixture is continuously inhaled. At some point, the inhalation of the rare gas mixture is discontinued and the decreasing value is monitored until transdermal respiration returns to equilibrium (the value prior to original inhalation). FIG. 1 shows a graph of concentration of transdermally diffused gas versus time. At time $T_0$, the gas mixture is administered to the mother. At time $T_1$, the gas is first detected in the suction cup by the gas analyzer. The gas mixture is continuously administered and the concentration of the gas transdermally diffused increases until a maximum value is reached at time $T_2$. This concentration value remains steady while the gas is continuously administered. At time $T_3$, the gas inhalation is discontinued and, at time $T_4$, the concentration value begins to decrease until, at time $T_5$, the equilibrium value is obtained. This provides three standard time values and a maximum maternal or fetal gas concentration value for maternal circulation or maternal-fetal circulation. Where two analyzers are employed simultaneously, values for both maternal circulation and fetal circulation can be obtained over the same time period. The first time value ($T_1$) is that of first detection, the second ($T_2$) is time to maximum concentration and the third ($T_5$ minus $T_3$) is time for return to equilibrium. Each of these values, as well as the maximum gas concentration values, can be compared to previously determined values for this individual or to standard values, as determined through the use of this method, to provide warnings of distress. Similarly, any sudden decrease in the plateau value is an indicator of distress. The decrease signifies a loss of transdermal diffusion, representative of blockage in the maternal-fetal circulatory system. An increase in diffusion would signify an improvement in maternal-fetal circulation, and possibly a relief of fetal distress.

EXAMPLE 2

The sheep of Example 1, prior to removal of the fetal lamb, was allowed to continuously inhale the 10% helium-90% oxygen mixture. The gas analyzer was operated continuously. First detection at the maternal skin using the described apparatus was at 18 seconds and a plateau was reached at 1 minute 55 seconds. A gas analyzer with a mass spectrometer was used to analyze the concentration of helium. After delivery of the fetal lamb, the experiment was re-initiated. The suction cup was attached to the fetal skin and first detection was at 38 seconds. The helium concentration rose over time until a plateau was reached at 2 minutes 56 seconds. The suction cup was removed from the fetal scalp, the gas mixture was discontinued, equilibrium was reobtained and the suction cup was placed on the maternal skin. Re-initiation of the helium-oxygen mixture resulted in first detection of helium at the maternal skin at 18 seconds with a plateau being reached at 1 minute 50 seconds.

In another embodiment, the invention comprises the use of a gas analyzer capable of detecting and analyzing multiple gases at one time. For example, the Leybold-Heraeus gas detectors known as the Inficon series are gas analyzers using mass spectrometers which are capable of detecting and analyzing plural gases at one time. Thus, while the methodolgy as outlined in various forms above is employed on the respiratory dynamics of inhaled rare gases, analysis can simultaneously be made of the normal transdermal respiration of physiological gases, such as oxygen and carbon dioxide. The corresponding concentration values can be monitored in the same manner as that of the rare gas in order to provide indications of distress. The normal physiological ranges of oxygen and carbon dioxide transdermal concentrations of these gases are well known for adult humans and newborn babies.

It is to be understood that the above embodiments are by way of example only and the total scope and delineation of the invention is as set out in the following claims. One skilled in the art would be expected to be able to substitute equivalent steps or instruments which, while not specifically enumerated or remarked upon in this body, are still encompassed by the spirit of the invention.

I claim:

1. A method for determining distress in a fetus comprising the steps of:
   A. Administering a predetermined concentration of gas to the mother;
   B. detecting transdermal diffusion of said gas at a location on the maternal skin;
   C. detecting transdermal diffusion of said gas at a location on the fetal skin;
   D. determining the time period from first administration of said gas to first detection of said gas transdermally diffused through the maternal skin;
   E. determining the time period from first administration of said gas to first detection of said gas transdermally diffused through the fetal skin; and
   F. Comparing said time periods to standard time period values.

2. The method of claim 1, further comprising the steps of:
   G. Repeating at selected time intervals the steps of administering, detecting, determining and comparing; and
   H. Comparing each newly determined time period to each previously determined time period.

3. The method of claim 2, further comprising the steps of:

I. Ascertaining a time value for fetal circulation by subtracting the time period for diffusion through the mother's skin from the time period for diffusion through the fetal skin.

4. The method of claim 1, where the step of administering said gas is performed by causing the mother to inhale said gas.

5. The method of claim 4, where the said gas is a rare gas and is administered in a concentration greater than the concentration of the gas in ambient air.

6. The method of claim 5, where said rare gas is helium, argon, krypton or neon.

7. The method of claim 1, where the steps of detecting transdermal diffusion of the gas are performed by attaching a gas detector means to the skin.

8. The method of claim 7, where the gas detector means is attached to the skin by contacting a suction cup onto the skin and maintaining sufficient suction to form a seal to preclude ambient air from entering the suction cup; where the suction cup is a conduit to the gas detector means for said transdermally diffused gas.

9. The method of claim 8, where the gas detector means comprises a mass spectrometer and vacuum pump.

10. The method of claim 7, where said gas detector means is simultaneously attached to both the maternal skin and the fetal skin.

11. The method of claim 7, where said gas detector means is a plural gas detector capable of detecting more than one gas simultaneously.

12. The method of claim 1, further comprising the step of:
  I. Monitoring the concentration level of said transdermally diffused gas over a continuing time period.

13. The method of claim 12, further comprising the steps of:
  J. Discontinuing the administration of said gas to the mother; and
  K. Monitoring the decline in concentration level of said transdermally diffused gas.

14. The method of claim 1, further comprising the steps of:

G. Ascertaining a time value for fetal circulation by subtracting the time period for diffusion through the mother's skin from the time period for diffusion through the fetal skin.

15. A method for determining fetal distress comprising the steps of:
  A. Attaching a suction cup to the mother's thigh, said suction cup providing a conduit for transdermally diffused gases to reach a gas detector means;
  B. Administering a mixture comprising oxygen and a rare gas by causing the mother to inhale the mixture, the percentage of rare gas in the mixture being higher than its normal percentage in ambient air;
  C. Detecting the presence of the rare gas diffused through the mother's skin;
  D. Determining the time period from first inhalation to first detection at the mother's skin;
  E. Attaching a suction cup to the scalp of the fetus;
  F. Detecting the presence of the rare gas diffused through the fetal scalp;
  G. Determining the time period from first inhalation until first detection at the fetal scalp; and
  H. Comparing the determined time periods to standard time period values.

16. The method of claim 15, further comprising the steps of:
  I. Repeating at selected time intervals the steps of administering, detecting and determining; and
  J. Comparing the time periods determined with each repetition to the time periods previously determined.

17. The method of claim 15, further comprising the steps of:
  I. Monitoring the concentration level of said transdermally diffused gas over a continuing time period.

18. The method of claim 17, further comprising the steps of:
  J. Discontinuing the administration of said gas mixture to the mother; and
  K. Monitoring the decline in concentration level of the diffused rare gas.

19. The method of claim 15, where said gas detector means comprises a mass spectrometer.

* * * * *